US009173836B2

(12) United States Patent
DiPiano et al.

(10) Patent No.: US 9,173,836 B2
(45) Date of Patent: Nov. 3, 2015

(54) PHARMACEUTICAL PREPARATIONS FOR TREATMENTS OF DISEASES AND DISORDERS OF THE BREAST

(75) Inventors: Gerianne Tringali DiPiano, Malvern, PA (US); Peter Kevin Mays, Philadelphia, PA (US); John Ziemniak, Gwynedd Valley, PA (US)

(73) Assignee: FemmeParma Holding Company, Inc., Wayne, PA (US)

( * ) Notice: Subject to any disclaimer, the term of this patent is extended or adjusted under 35 U.S.C. 154(b) by 452 days.

(21) Appl. No.: 12/871,678

(22) Filed: Aug. 30, 2010

(65) Prior Publication Data

US 2011/0212934 A1 Sep. 1, 2011

Related U.S. Application Data

(63) Continuation-in-part of application No. 10/751,056, filed on Jan. 2, 2004, now Pat. No. 7,812,010.

(60) Provisional application No. 60/437,778, filed on Jan. 2, 2003.

(51) Int. Cl.
| | |
|---|---|
| *A61K 31/58* | (2006.01) |
| *A61P 15/00* | (2006.01) |
| *A61P 21/00* | (2006.01) |
| *A61K 38/09* | (2006.01) |
| *A61K 31/137* | (2006.01) |
| *A61K 9/00* | (2006.01) |
| *A61K 9/06* | (2006.01) |
| *A61K 31/445* | (2006.01) |
| *A61K 47/10* | (2006.01) |
| *A61K 47/22* | (2006.01) |

(52) U.S. Cl.
CPC ............. *A61K 9/0014* (2013.01); *A61K 9/0041* (2013.01); *A61K 9/06* (2013.01); *A61K 31/445* (2013.01); *A61K 47/10* (2013.01); *A61K 47/22* (2013.01)

(58) Field of Classification Search
None
See application file for complete search history.

(56) References Cited

U.S. PATENT DOCUMENTS

| | | | |
|---|---|---|---|
| 3,921,636 A | 11/1975 | Zaffaroni | |
| 3,927,216 A | 12/1975 | Witkowski | |
| 4,081,533 A | 3/1978 | Cheesman | |
| 4,107,288 A | 8/1978 | Oppenheim | |
| 4,272,398 A | 6/1981 | Jaffe | |
| 4,286,587 A | 9/1981 | Wong | |
| 4,291,028 A | 9/1981 | Vorys | |
| 4,292,315 A | 9/1981 | Vorys | |
| 4,391,797 A | 7/1983 | Folkman | |
| 4,524,359 A | 6/1985 | Champagne | |
| 4,525,340 A | 6/1985 | Lange | |
| 4,588,724 A | 5/1986 | Greenway, III | |
| 4,591,496 A | 5/1986 | Cohen | |
| 4,673,405 A | 6/1987 | Guittard | |
| 4,756,907 A | 7/1988 | Beck | |
| 4,762,717 A | 8/1988 | Crowley, Jr. | |
| 4,826,830 A | 5/1989 | Han | |
| 4,861,627 A | 8/1989 | Mathiowitz | |
| 4,873,092 A | 10/1989 | Azuma | |
| 4,919,937 A | 4/1990 | MauvaisJarvis | |
| 4,919,939 A | 4/1990 | Baker | |
| 4,965,128 A | 10/1990 | Greidanus | |
| 4,997,653 A | 3/1991 | Igarashi | |
| 5,057,317 A | 10/1991 | Iida | |
| 5,066,495 A | 11/1991 | Moro | |
| 5,091,185 A | 2/1992 | Castillo | |
| 5,130,137 A | 7/1992 | Crowley, Jr. | |
| 5,145,684 A | 9/1992 | Liversidge | |
| 5,156,851 A | 10/1992 | Castillo | |
| 5,194,259 A | 3/1993 | Soudant | |
| 5,324,522 A | 6/1994 | Krenning | |
| 5,330,768 A | 7/1994 | Park | |
| 5,340,585 A | 8/1994 | Pike | |
| 5,359,030 A | 10/1994 | Ekwuribe | |
| 5,362,720 A | 11/1994 | Labrie | |
| 5,413,797 A | 5/1995 | Khan | |
| 5,417,982 A | 5/1995 | Modi | |

(Continued)

FOREIGN PATENT DOCUMENTS

| | | |
|---|---|---|
| DE | 10054294 | 5/2002 |
| EP | 0501056 | 9/1992 |

(Continued)

OTHER PUBLICATIONS

Mansel et al. In the Lancet, 928-930 (1982).*
O'Brien et al. In American Journal of Obstetrics and Gynecology 1999; 180:18-23.*
'Goserelin Acetate' (ChemicalProductProperty_EN_CB128102) accessed from the internet on Oct. 26, 2012.*
Hamed et al. In Annals of the Royal College of Surgeons of England (1990) 72, 221-224.*
Definition systemic (thefreedictionary.com/systemic) accessed from the internet on Oct. 26, 2012.*
Levin, et al., "Effectiveness of vaginally administered oxybutynin on rabbit bladder function", Urology, 61(6):1273-77 (2003).

(Continued)

*Primary Examiner* — Dennis Heyer
(74) *Attorney, Agent, or Firm* — Pabst Patent Group LLP

(57) ABSTRACT

Formulations for topical or local administration of drugs directly to the breast or chest to produce a regional or local effect with lower systemic drug levels than when an effective amount is administered systemically are disclosed herein. In a preferred embodiment, the drug is administered to the surface of the breast, areola, or directly to the nipple. The formulations provide increased patient comfort, increased bioavailability and relatively high blood levels in the region to be treated with a reduction of side effects compared to those administered systemically. The preferred formulations contain drugs in the form of micro or nanoparticles, which may be formed of drug alone or in combination with an excipient or carrier. The excipient or carrier may modify the release rates or enhance absorption into the affected area. The drug formulation may be in the form of a cream, lotion or foam.

13 Claims, 1 Drawing Sheet

(56) References Cited

U.S. PATENT DOCUMENTS

| | | | |
|---|---|---|---|
| 5,434,146 A | 7/1995 | Labrie | |
| 5,438,040 A | 8/1995 | Ekwuribe | |
| 5,472,704 A | 12/1995 | Santus | |
| 5,482,925 A | 1/1996 | Hutsell | |
| 5,482,927 A | 1/1996 | Maniar | |
| 5,494,047 A | 2/1996 | VanOs | |
| 5,510,118 A | 4/1996 | Bosch | |
| 5,536,499 A | 7/1996 | Znaiden | |
| 5,552,160 A | 9/1996 | Liversidge | |
| 5,580,857 A | 12/1996 | Oden | |
| 5,614,212 A | 3/1997 | DAngelo | |
| 5,633,011 A | 5/1997 | Dong | |
| 5,643,604 A | 7/1997 | Angeles Uribe | |
| 5,651,976 A | 7/1997 | Price | |
| 5,705,170 A | 1/1998 | Kong | |
| 5,778,894 A | 7/1998 | Dorogi | |
| 5,789,442 A | 8/1998 | Garfield | |
| 5,843,509 A | 12/1998 | CalvoSalve | |
| 5,843,979 A | 12/1998 | Wille | |
| 5,945,109 A | 8/1999 | Schmidt | |
| 5,993,856 A * | 11/1999 | Ragavan et al. | 424/489 |
| 6,071,526 A | 6/2000 | Schmidt | |
| 6,083,996 A * | 7/2000 | Buyuktimkin et al. | 514/772.6 |
| 6,087,351 A | 7/2000 | Nyce | |
| 6,358,539 B1 | 3/2002 | Murad | |
| 6,416,778 B1 | 7/2002 | Ragavan | |
| 6,436,428 B1 | 8/2002 | Mahashabde | |
| 6,482,448 B2 | 11/2002 | Tabor | |
| 6,517,864 B1 | 2/2003 | OrupJacobsen | |
| 6,652,874 B2 | 11/2003 | Ragavan | |
| 6,743,441 B2 | 6/2004 | Sanders | |
| 6,908,623 B2 | 6/2005 | Deaver | |
| 2002/0150605 A1 | 10/2002 | Yui | |
| 2003/0109507 A1 | 6/2003 | Franke | |
| 2003/0143278 A1 | 7/2003 | DiPiano | |
| 2003/0153585 A1 | 8/2003 | Schreder | |
| 2003/0175329 A1 | 9/2003 | Azarnoff | |
| 2004/0002503 A1 | 1/2004 | Chang | |
| 2004/0018991 A1 | 1/2004 | Schmidt | |
| 2004/0138314 A1 | 7/2004 | Bua | |
| 2005/0101579 A1 | 5/2005 | Shippen | |
| 2005/0250805 A1 | 11/2005 | Kannan | |
| 2008/0153789 A1 | 6/2008 | Dmowski | |
| 2008/0299207 A1 | 12/2008 | Martin | |

FOREIGN PATENT DOCUMENTS

| | | |
|---|---|---|
| EP | 0566135 | 10/1993 |
| FR | 2843303 | 2/2004 |
| GB | 767824 | 2/1957 |
| GB | 2420281 | 5/2006 |
| JP | 61063615 | 4/1986 |
| JP | 61500914 | 5/1986 |
| JP | 62187415 | 8/1987 |
| JP | 03090029 | 4/1991 |
| JP | 72670 | 2/1994 |
| JP | 2002520272 | 7/2002 |
| WO | 9112007 | 8/1991 |
| WO | 9507071 | 3/1995 |
| WO | 9531973 | 11/1995 |
| WO | 9531974 | 11/1995 |
| WO | 9600567 | 1/1996 |
| WO | 9625150 | 8/1996 |
| WO | 9637232 | 11/1996 |
| WO | 9729735 | 8/1997 |
| WO | 9811888 | 3/1998 |
| WO | 9832422 | 7/1998 |
| WO | 9924041 | 6/1999 |
| WO | 0027372 | 5/2000 |
| WO | 0072883 | 12/2000 |
| WO | 0217926 | 3/2002 |
| WO | 03039553 | 5/2003 |
| WO | 03053292 | 7/2003 |
| WO | 2004060322 | 7/2004 |
| WO | WO 2004/060322 * | 7/2004 |
| WO | 2008083158 | 7/2008 |

OTHER PUBLICATIONS

Akio, "Danazol Suppository", Patent Abstracts of Japan 15(263): (C-0847) (1991).

Anderson, et al, 'Once daily controlled versus immediate release oxybutynin chloride for urge urinary incontinence. OROSOxybutynin Study Group,' J. Urol. 161: 1809-1812 (1999).

Barnhart, et al., 'Distribution of a spermicide containing Nonoxynol-9 in the vaginal canal and the upper female reproductive tract', Hum Reprod,.16(6):1151-4 (2001).

Benita, et al., "Characterization of drug-loaded poly(d,l-lactide) microspheres," J Pharm Sci 73(12): 1721-1724 (1984).

Braun, et al, Effect of danazol in vitro and in viva on monocyte-mediated enhancement of endometrial cell proliferation in women with endometriosis: Fertility and Sterility 62(1): 89-95 (1994).

Brendler, et al., 'Topical oxybutynin chloride for relaxation of dysfunctional bladders,' J. Urol. 141(6): 1350-52 (1989).

Buyse, et al., 'Intravesical oxybutynin for neurogenic bladder dysfunction: less systemic side effects due to reduced first pass metabolism,' J. 1.1rot 160: 892-896 (1998).

Chan, et al., "Breast pain: What to do?", The Hong Kong Practitioner, 21:573-578 (1999).

Cicinelli, et al., 'First uterine pass effect is observed when estradiol is placed in the upper buy not lower third of the vagina', Fertility and Steriility, 81(5):1414-1416 (2004).

Colacurci, et al., "Effects of tibolone on the breast", Eur. J. Obstet. Gynecol. Reprod. Biol., 80(2):235-8 (1998).

Comer & Goa, "Extended-release oxybutynin," Drugs Aging 16: 149-155 (2000).

Das Neves, et al., "Gels as vaginal drug delivery systems", Int. J. Pharm. 2:318 (1-2)1-14 (2006) Epub Mar. 17, 2006.

De Ziegler, et al., 'Administration non-orate de la progesterone: Experiences et avenir de la vole transvaginale,' Rev. Med. Suisse Romande pp. 13#2D(s#(1994) (with English Abstract).

Farquhar, et al., "Management of dysfunctional uterine bleeding," Drugs 44(4): 378-384 (1992).

Femmepharma, "FP1096-001 Executive Summary," (2004).

Fentiman, et al. 'Tamoxifen and benign breast problems.', Lancet, 2(8567) 1070-1072 (1987).

Fentiman, et al., 'Dosage and duration of tamoxifen treatment for mastalgia: a controlled trial,' Br J Surg. 75(9): 845 846 (1988).

Fentiman, et al., 'Studies of tamoxifen in women with mastalgia,' Br. J. Clinical Prac. Sympt 68: 34-36 (1989).

Finnin and Morgan, 'Transdermal penetration enhancers: applications, limitations, and potential', J. Pharm. Sci.,88(10):955-8 (1999).

Geraghty, et al., 'The in vitro release of some antimuscarinic drugs from monoolein/water lyotropic crystalline gels,' Pharm.Res. 13(8): 1265-1271 (1996).

Goldenberg, 'An extended-release formulation of oxybutynin chloride for the treatment of overactive urinary bladder,' Din. Ther. 21(4): 634-642 (1999).

Guerriero, et al., Influence of vaginal danazol on uterine and brain perfusion during hormonal replacement therapy,Menopause, 8(6); 424-428 (2001) (abstract only).

Gupta & Sathyan, 'Pharmacokinetics of an oral once-a-day controlled-release oxybutynin formulation compared with immediate-release oxybutynin,' J. Olin. Pharmacal. 39: 289-296 (1999).

Hinton, et al., 'A double-blind controlled trial of danazol and bromocriptine in the management of severe cyclical breast pain', Br. J. Ciin. Practice 40(8): 326-330 (1986).

Holland & Gateley, "Drug therapy of mastalgia. What are the options?" Drugs 48(5): 709-716 (1994).

Hull, et al., "Endometriosis: An enigmatic disease," J Women's Health 5(2): 111-120 (1996).

Igarashi, 'A new therapy for pelvic endometriosis and uterien adenomysosis: Local effect of vaginal and intrauterinedanazol application,' Asia-Oceania J. Obstet. Gynaecol. 16(1): 1-12 (1990).

(56) References Cited

OTHER PUBLICATIONS

Irvin & Morrison, 'Effectiveness of topical non-steroidal anti-inflammatory drugs in the management of breast pain,',J. R. Coll. Edinb. 43(3): 158-159 (1998).
Leonard, et al., 'Randomized, double-blind, placebo-controlled, multi center trial of 6% miltefosine solution, a topical chemotherapy in cutaneous metastases from breast cancer,' J. Clin. Oncol. 19: 4150-4159 (2001).
Lim, et al., 'Microencapsulation of living cells and tissues,' J Pharm. Sci. 70(4): 351-354 (1981).
Liversidge, et al., 'Particle size reduction for improvement of oral bioavailability of hydrophobic drugs: I. Absolute oralbioavailability of nanocrystalline danazol in beagle dogs', Int J Pharm., 125:91-97 (1995).
Lobo, et al., 'Vaginal route paradox: A direct transport to the uterus,' Symposium: The First Uterine Pass Effect, Wyeth Ayerst International, Inc. (1995).
Lufkin and Ory, 'Relative value of transdermal and oral estrogen therapy in various clinical situations', Mayo Clin. Proc., 69(2):1315 (1994).
Mansel, et al., 'A double blind trial of the prolactin inhibitor bromocriptine in painful benign breast disease,' Br. J.Surgery 65(10): 724-27 (1978).
Mansel, et al., 'Controlled trial of the antigonadotropin danazol in painful nodular benign breast disease,' Lancet 1(8278): 928-933 (1982).
Mansel & Dogliotti, European multicentre trial of bromocriptine in cyclical mastaigia: Lancet 335(868): 190-193(1990).
Massad, et al., 'The pharmacokinetics of intravesical and oral oxybutynin chloride,' J. Urol. 148: 595-597 (1992).
Mathiowitz, et al, Novel microcapsules for delivery systems, Reactive Polymers 6: 275-283 (1987).
Mathiowitz, et al., 'Morphology of polyanhydride microsphere delivery system,' Scanning Microscopy 4(2): 329-340(1990).
Mathiowitz, et al., 'Poiyanhydride microshperes as drug carriers I. Hot-melt microencapsulation,' J Controlled Release 5:13-22 (1987).
Mathiowitz, et al., 'Polyanhydride microspheres as drug carriers. II. Microencapsualtion by solvent removal,' J Appl.Polymer Sci. 35: 755-774 (1988).
Millet & Dirbas, 'Clinical management of breast pain: a review,' Obstet. Gynecol. Survey 57(7): 451-461 (2002).
Mizutani, et al, 'Danazol concentration in ovary, uterus, and serum and their effect on the hypothalamic-pituitary ovarian axis during vaginal administration of a danazol suppository,' Fertility and Sterility 63(6): 1184-1189 (1995).
Moline, 'Pharmacologic strategies for managing premenstrual syndrome', Clin. Pharm., 12(3):181-96 (1993).
Montgomery, et al., 'Treatment of severe cyclical mastalgia', J. R. Soc. Med., 72(7):489-491 (1979).
Nazli, et al, "Controlled trial of the prolactin inhibitor bromocriptine (Parlodel) in the treatment of severe cyclicalmastalgia," Br J Clin Pract 43: 322-327 (1989).
Physicians' Desk Reference, Consult 1994 Supplements for Revisions, pp. 1372-1375.
Plu-Bureau, et al, 'Percutaneous progesterone use and risk of breast cancer: results from a French cohort study of premenopausal women with benign breast disease', Cancer Detect. Prev., 23(4):290-6 (1999).
Ramjee, et al., 'Acceptability of Carraguard, a candidate microbicide and methyl cellulose placebo vaginal gels among HIV-positive women and men in Durban, South Africa', AIDS Res Ther. 4:20 pp. 1-10 (2007).

Saito, et al., 'Treatment of overactive bladder with modified intravesical oxybutynin chloride,' Neural. Urodyn. 19: 683 688 (2000).
Salib, et al., 'Utilization of sodium alginate in drug microencapsulation,' Pharmazeutische Industrie 40(11A):1230-1234(1978).
Schroder, et al., 'Absorption of oxybutinin from vaginal inserts: drug blood levels and the response of the rabbit bladder, 'Urology 56(6): 1063-1067 (2000).
Spooner, Classification of Side Effects to Danazol Therapy, Winthrop Laboratories, Surrey, England, Dated 1977.
Steinbrunn, et al., 'Mastalgia. Tailoring treatment to type of breast pain,' Postgraduate Medicine 102(5): 183-184; 187-187; 193-194 (1997). 'Sultrin,' Physicians' Desk Reference, 51st ed., pp. 1941 (1997).
Takebayashi, at al., 'Danazol suspension injected into the uterine cervix of patients with adenomyosis and myoma. Preliminary study', Gynecol. Obstet. Invest., 39(3):207-11 (1995) (abstract only).
'Terazol 7,' Physicians' Desk Reference, 51st ed., pp. 1943 (1997).
Terazol 7, Physicians' Desk Reference, 51st ed., pp. 1943 (1997).
Terwogt, et al 'Phase II trial of topically applied miltefosine solution in patients with skin-metastasized breast cancer,' Br. J. Cancer 79: 1158-1161 (1999).
The First Uterine Pass Effect a new finding for new options in progesterone therapy, West-Ayerst hternation, Inc. (1995).
Thuroff, et al., 'Randomized, double-blind, multicenter trial on treatment of frequency, urgency and incontinence related to detrusor hyperactivity: oxybutynin versus propantheline versus placebo,' J. Uml. 145: 813-816 (1991).
Unger, et al., "Hexadecylphosphocholine in the topical treatment of skin metastases in breast cancer patients," Cancer Treat. Rev. 17: 243-246 (1990).
Versi, et al., 'Dry mouth with conventional and controlled-release oxybutynin in urinary incontinence,' Obstet Gynecol. 95(5): 718-721 (2000).
Wagner, at al., 'The novel progesterone receptor antagonists RT13021-012 and RT13021-022 exhibit complex glucocorticoid receptor antagonist activities: implications for the development of dissociated antiprogestins', Endocrinology, 140(3):1449-58 (1999).
Wellbery, et al., 'Diagnosis and treatment of endometriosis', Am. Fam. Physician, 60:1753-68 (1999).
Wolthers Kluwer Health, Inc., "Summary Review: Oxybutynin Chloride 10 % Gel" , Wolthers Kluwer Health, Inc., (2009).
Yamashita, et al., Immunohistochemical determination of endometrial progesterone receptor (PR) content after intrauterine infusion of danazol in rabbits, Nippon Naibunpi Gakkai Zasshi, 69 (10):1044-1050 (1993) (abstract only).
Zhang, et al., 'Synthesis and progesterone receptor antagonist activities of 6-aryl benzimidazolones and benzothiazolones', Bioorg. Med. Chem. Lett., 11 (20):2747-50 (2001).
"Sultrin," Physicians\ Desk Reference, 51st ed., pp. 1941 (1997).
Gateley, et al., "Drug treatments for mastalgia: 17 years experience in the Cardiff Mastalgia Clinic" , J R Soc Med., 85(1)12-15 (1992).
Musich, et al., "Estrogenic and antiestrogenic effects of danazol administration in studies of estradiol receptor binding" , Am J Obstet Gynecol., 40(1):62-9 (1981).
Tamaya, et al., "Danazol binding to steroid receptors in human uterine endometrium" , Fertil. Steril., 41(5):732-5 (1984).
Wada, et al., "Estrogen binding sites in peripheral blood monocytes and effects of danazol on their sites in vitro" , Gen. Pharmacol., 23(4):693-700 (1992).
Soe, et al., "Tissue distribution of transdermal toremifene" , Cancer Chemother Pharmacol., 39(6):513-20 (19979).

* cited by examiner

PHARMACEUTICAL PREPARATIONS FOR TREATMENTS OF DISEASES AND DISORDERS OF THE BREAST

CROSS-REFERENCE TO RELATED APPLICATIONS

This application is a continuation-in-part of U.S. patent application Ser. No. 10/751,056, filed Jan. 2, 2004, which claims benefit of and priority to U.S. Ser. No. 60/437,778, filed Jan. 2, 2003, entitled "Pharmaceutical Preparations for Treatments of Diseases and Disorders of the Breast", both of which are incorporated by reference in their entirety.

FIELD OF INVENTION

The present invention relates to pharmaceutical preparations for the treatment of diseases and disorders of the breast, chest and underlying musculature.

BACKGROUND OF THE INVENTION

Breast disorders are so common that B. Smith & W. Souba, *Breast disease*, p. 1, in *Breast Disease* 2, D. Wilmore, et al. (eds) (New York, Scientific America) (1995) estimate that one of every two women will consult her physician about a breast disorder at some point in her life. Clinically, the most useful classification system for benign breast disease is based on symptoms and physical findings. The six general categories of symptoms are:
1. Physiologic swelling and tenderness;
2. Nodularity, significant lumpiness, both cyclic and non-cyclic;
3. Mastalgia, severe pain, both cyclic and non-cyclic;
4. Dominant lumps, including gross lumps and fibroadenomas;
5. Nipple discharge, including intraductal papilloma and duct ectasia; and
6. Infections and inflammation, including subareolar, abscesses, lactational mastitis, breast abscesses and Mondor's Disease. See J. Isaacs, *Benign Neoplasms*, in D. Marchant, *Breast Disease*, p. 65-68 (WB Saunders, Philadelphia, Pa.) (1997).

Swelling, breast pain, and nodularity (Categories 1 and 2) are often grouped together and referred to as fibrocystic disease or changes. However, aggregating these categories may be problematic as the various causes of these symptoms may be isolated to determine the specific cause of the condition and the resultant treatment option to be undertaken. For example, women on oral contraceptives or hormone replacement therapy may experience swelling and breast tenderness (Category 1). By reducing or eliminating the estrogen replacement therapy, the breast pain or swelling may be reduced. Alternatively, breast pain may be caused by trauma, chest wall pain, or by costochondritis.

Dominant lumps (Category 4) are generally clinically benign breast lesions that are distinct, persistent, and relatively unchanging. The lesions that are represented by these lumps include macrocysts, galactoceles, and fibroadenomas. These lumps generally do not respond to hormonal therapy that may be effective in treating nodularity or breast pain.

Fibroadenomas (Category 4) represent the most common benign solid tumor of the female breast. They are typically seen in women in the third decade of life although they are sometimes seen in postmenopausal women. Fibroadenomas may respond to hormonal therapy and may change in size throughout the menstrual cycle.

Treatment options for breast disorders fall into two major categories, pharmacologic therapy and surgical approaches. Before initiating any treatment, an assessment of dietary, hormone therapy and other factors must be taken into consideration. Women who use estrogen replacement therapy or oral contraceptives may discontinue therapy. In addition, dietary modification such as a reduction in saturated fat intake and caffeine consumption may reduce breast pain in certain women.

Drug treatment for breast pain is tailored to the severity of pain, chances of improvement with each drug, and potential adverse effects. P. Holland & C. Gately, *Drugs*, 48(5):709-716 (1994). Women with mild pain may be administered 6-8 capsules of gamma-linolenic acid (also known as "gamolenic acid" or "GLA") (40 mg) per day. The side effects associated with GLA are mild. For severe pain, the only approved treatment option is danazol, which is typically given in a dose of 100 mg to 200 mg per day. Danazol is highly effective, although it causes androgenic side effects which may reduce patient compliance. Controlled trials demonstrate that at oral doses of 200 mg to 400 mg per day, danazol produces a favorable clinical response in 70% to 80% of patients. C. Hinton, et al., *British J. Clinical Practice*, 40(8):326-30 (1986); R. Mansel, et al., *Lancet*, 8278: 928-933 (1982); and B. Steinbrum, et al., *Postgraduate Medicine*, 102(5):183-84, 187-87, and 193-94 (1997). In most instances, breast pain and tenderness are significantly relieved by the first month and eliminated in two to three months. Usually elimination of nodularity requires four to six months of therapy. However, high doses of danazol result in adverse side effects, which may include weight gain, voice change, development of facial and chest hair, loss of libido, acne, and central nervous system ("CNS") symptoms such as depression, anxiety, fatigue, nausea and diarrhea, as well as the inhibition of pregnancy while undergoing treatment. See e.g. Spooner, *Classification of Side Effects to Danazol Therapy*, Winthrop Laboratories, Surrey, England.

Bromocriptine, tamoxifen, and luteinizing hormone-releasing hormone (LHRH) analogues are not approved for the initial treatment of breast pain and fibrocystic breast disease, but are used to treat breast pain and fibrocystic disease that are resistant to other forms of treatment. The side effects associated with these drugs are severe.

Bromocriptine, which inhibits release of prolactin, is effective in up to 65% of women treated for cyclical mastalgia, i.e. breast pain which occurs in a regular pattern over time, at doses of 5 mg per day. These results were confirmed in a multicenter, randomized, controlled study. K. Nazli et al., *Br J Clin Pract.*, 43: 322-27 (1989); R. Mansel & L. Dogliotti, *Lancet*, 335 (868):190-193 (1990). Improvement in symptoms was accompanied by a decrease in serum prolactin level. Mild side effects, including nausea, dizziness, headaches, and irritability have been reported in 30% of women, and 10% have complained of more severe side effects. These side effects can be minimized by altering the dosing regimen or reducing the amount of drug administered. However, R. Mansel et al., *BR J Surgery*, 65(10):724-27 (1978) noted that bromocriptine did not induce a response in patients with non-cyclical breast pain.

In severe cases of breast pain and fibrocystic breast disease, tamoxifen has been prescribed. Controlled trials demonstrated 80% to 90% success in treatment of cyclical mastalgia. I. Fentimen, et al., *Br. J. Clinical Prac. Sympt.*, 68:34-36 (1989). In addition, no difference in response was noted in women who received daily doses of 10 mg per day versus those who received daily doses of 20 mg per day. A decrease in side effects was noted however, in women who received 10 mg per day. I. Fentimen, et al., *BR J Surg.*, 75(9): 845-46 (1988).

Non-steroidal anti-inflammatory drugs (NSAIDs) are sometimes prescribed for the treatment of breast pain. A prospective study of the effectiveness of the topical application of NSAIDs as a gel formulation was carried out in 26 women with severe breast pain. A topical NSAID gel was applied as required and provided rapid relief of pain with no side effects in 81% of the women. A. Irving & S. Morrison, *JR Coll Edinb*, 43(3):158-9 (1998).

In non-cyclical mastalgia, and especially for chest wall pain, injections of lidocaine 1% (1 ml) and methylprednisone (40 mg) have been shown to be effective. Response rates of 90% have been reported, but about 50% of patients required a second injection 2 to 3 months later. A. Millet & F. Dirbas, *Obstetrical and Gynecological Survey*, 57(7): 459 (2002).

Miltefosine (also known as MILTEX® and hexadecylphosphocholine) has been used topically to treat cutaneous manifestations of metastatic breast cancer. See e.g. C. Unger et al., *Cancer Treat Rev* 17: 243-246 (1990); J. Terwogt et al., *Br J Cancer*, 79: 1158-1161 (1999); and R. Leonard et al., *J Clin Oncol*, 19: 4150-4159 (2001). These reports indicate that the cytostatic drug, miltefosine, is useful to treat topical lesions arising from a primary neoplasia event in the breast. However, the drug does not treat neoplastic lesions within the breast tissue and the cutaneous metastatic tissue need not be localized to breast skin. Therefore, the drug is merely acting topically at the site of administration. Further, the drug is not effective at treating the underlying disease of the breast.

Treatment of disorders and diseases of the breast and underlying musculature by traditional methods of oral or systemic administration is associated with a significant number of side effects and other complications that limit their use. For example, the normal digestive process may reduce bioavailability of drugs, requiring a higher dose be administered in order to achieve the desired effect. In addition, passage of the drag from the liver into the systemic circulation may convert the drug into a metabolite of the drug and cause a variety of untoward side effects. Either of these problems may cause patients to avoid their medications and disregard their doctors' treatment regimes.

It is therefore an object of the present invention to provide formulations and methods of administration to increase patient compliance and comfort during the treatment of diseases and disorders of the breast and chest.

It is a further object of the present invention increase the bioavailability of drug administered topically to the breast or chest as compared to drugs administered systemically.

BRIEF SUMMARY OF THE INVENTION

Formulations for topical or local administration of drugs other than non-steroidal antiinflammatories or analgesics such as lidocaine, such as hormones (and hormone releasing compounds) and analogs thereof, and chemotherapeutic agents, directly to the breast or chest to produce a regional or local effect with lower systemic drug levels than when an effective amount is administered systemically are disclosed herein. In a preferred embodiment, the drug is administered to the surface of the breast, areola, or directly to the nipple. The formulations provide increased patient comfort, increased bioavailability and relatively high blood levels in the region to be treated and have reduced side effects compared to when the same drugs are administered systemically. The preferred formulations contain drugs in the form of micro or nanoparticles, which may be formed of drug alone or in combination with an excipient or carrier. The excipient or carrier may modify the release rates or enhance absorption into the affected area. The drug formulation may be in the form of a cream, lotion or foam.

DETAILED DESCRIPTION OF THE INVENTION

Figure 1:
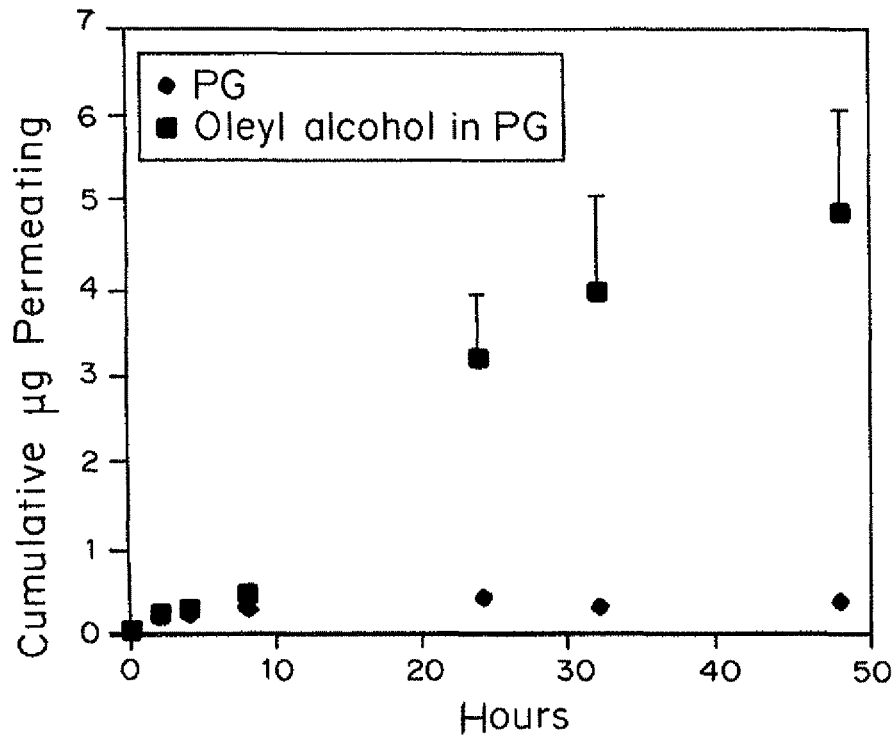
FIG. 1 is a graph of time (hours) versus cumulative amount of danazol permeating through the breast skin (μg) for two different formulations, one containing propylene glycol as the carrier (◇) and the other containing propylene glycol and 5% oleyl alcohol as the carrier (■).

The compositions and methods for administration thereof provide for significantly diminished side effects with increased bioavailability, as compared to systemic drug administration techniques.

As used herein, "locally" refers to delivery generally to the surface of the breast or chest and to the tissue immediately below the surface of the breast chest. As used herein, "regionally" refers to the general application site and its interrelated surrounding tissues. As used herein, "systemically" generally refers to the circulatory system and regions outside the spaces described above.

I. Formulations

The formulations are designed to provide maximum uptake in the affected tissues with rapid dissemination throughout the region to be treated, with little to no increase in systemic blood levels of the drug. In a preferred embodiment the active agent is dissolved in a solution. For insoluble active agents, additional agents may be added to the formulation to increase solubility.

The formulation may include drug alone or in combination with excipients, carriers, and/or penetration enhancers. Excipients for topical administration may include: (a) antimicrobial compounds, e.g. parabens, (b) antioxidants, e.g. sodium ascorbyl acetate and alpha-tocopherol, (c) stabilizers, e.g. sorbitol, or (d) emulsifying agents to produce a stable emulsion with both a hydrophilic and a hydrophobic phase. In the preferred embodiment, the formulation is applied topically and is transdermally delivered to the tissue in need of treatment.

A. Active Agents

The term "drug" as generally used herein refers to any pharmacologically active substance capable of eliciting a desired alteration to a physiological system. The formulations may contain one or more active agents. Drugs may be synthetic or isolated natural compounds, proteins or peptides, antibodies, oligonucleotides or nucleotides, polysaccharides or sugars, or complexes of any of the above. Drugs may have a variety of activities, which may be inhibitory or stimulatory, including antibiotic, antiviral, antifungal, steroidal, cytotoxic, and anti-proliferative effects.

Other suitable active agents include media contrast agents and other diagnostic agents. Diagnostic agents may be delivered in the formulations to aid in disease diagnosis. A description of the various classes of suitable pharmacological agents and drugs may be found in Goodman and Gilman, *The Pharmacological Basis of Therapeutics*, (9th Ed., McGraw-Hill Publishing Co.) (1996).

In the preferred embodiment, the drug is a chemotherapeutic such as danazol, bromocriptine, or tamoxifen, or a hormone, hormone releasing agent, or analog thereof such as a LHRH analogue or an antiestrogen. In the most preferred embodiment, the active agent is danazol, an isoxazolo derivative of 17∝ ethenyltestosterone (an androgen hormone).

B. Excipients or Carriers

The drug is delivered to the breast tissue via local, topical or percutaneous delivery with suitable excipients or carriers to enable and/or enhance drug penetration. Suitable carriers or excipients may enhance the physical and chemical stability of the formulation or enhance its aesthetic properties.

The carrier may be any gel, ointment, lotion, emulsion, cream, foam, mousse, liquid, spray, or aerosol which is capable of delivering the drug to the breast tissue. In the local drug delivery vehicles described herein, a compounding agent, co-solvent, surfactant, emulsifier, antioxidant, preservative, stabilizer, or diluent may be included in the formulation. A suitable emulsifying agent is needed if the active agent is insoluble in an aqueous environment. A penetration enhancer may be added to enable the active agent to cross the barrier of the stratum corneum. In the preferred embodiment, the carrier is a gel, which is odorless and tasteless and dissolves rapidly, such as a hydroalcoholic gel.

Diluents may be included in the formulations to dissolve, disperse or otherwise incorporate the carrier. Examples of diluents include, but are not limited to, water, buffered aqueous solutions, organic hydrophilic diluents, such as monovalent alcohols, and low molecular weight glycols and polyols (e.g. propylene glycol, polypropylene glycol, glycerol, butylene glycol).

Appropriate excipients are selected based on the active agent and the type of the formulation. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars, and starches.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof.

Buffers can be used to control pH of the formulation. Preferably, the buffers buffer the formulation from a pH of about 4 to a pH of about 7.5, more preferably from a pH of about 4 to a pH of about 7, and most preferably from a pH of about 5 to a pH of about 7. In a preferred embodiment, the buffer is triethanolamine.

C. Penetration Enhancers

Penetration enhancers are frequently used to promote transdermal delivery of drugs across the skin, in particular across the stratum corneum. Some penetration enhancers cause dermal irritation, dermal toxicity and dermal allergies. However, the more commonly used ones include urea, (carbonyldiamide), imidurea, N,N-diethylformamide, N-methyl-2-pyrrolidone, 1-dodecal-azacycloheptane-2-one, calcium thioglycate, 2-pyrrolidone, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10 oxyethylene ether), BRIJ® 78 (stearyl poly(20)oxyethylene ether), BRIJ® 96 (oleyl poly(10)oxyethylene ether), and BRIJ® 721 (stearyl poly (21) oxyethylene ether) (ICI Americas Inc. Corp.).

D. Gels

In preferred embodiments, the formulation is a gel. A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Examples of the composition of danazol gels are shown in the examples. The gelling agent can be natural, semi-synthetic, or synthetic. Suitable thickening or gelling agents include, but are not limited to, acacia, acrylates/steareth-20 methacrylate copolymer, agar, algin, alginic acid, ammonium acrylate copolymers, ammonium alginate, ammonium chloride, ammonium sulfate, amylopectin, attapulgite, bentonite, $C_9$-$C_{15}$ alcohols, calcium acetate, calcium alginate, calcium carrageenan, calcium chloride, caprylic alcohol, vinyl polymers such as cross linked acrylic acid polymers with the name carbomer, such as but not limited to carbomer 910, carbomer 934, carbomer 934P, carbomer 940, carbomer 941; modified celluloses such as hydroxypropyl cellulose and hydroxyethyl cellulose; Carbopol homopolymers and copolymers, carboxymethyl hydroxyethylcellulose, carboxymethyl hydroxypropyl guar, carrageenan, cellulose, cellulose gum, cetearyl alcohol, cetyl alcohol, corn starch, damar, dextrin, dibenzylidine sorbitol, ethylene dihydrogenated tallowamide, ethylene dioleamide, ethylene distearamide, gelatin, guar gum, hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, hydroxypropylcellulose, hydroxypropyl guar, hydroxypropyl methylcellulose, isocetyl alcohol, isostearyl alcohol, karaya gum, kelp, lauryl alcohol, locust bean gum, magnesium aluminum silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M is also known as Polyox WSR® N-IO, which is available from Union Carbide and as PEG-2,000; PEG-5M is also known as Polyox WSR® N-35 and Polyox WSR® N-80, both available from Union Carbide and as PEG-5,000 and Polyethylene Glycol 300,000; PEG-7M is also known as Polyox WSR® N-750 available from Union Carbide; PEG 9-M is also known as Polyox WSR® N-3333 available from Union Carbide; PEG-14M is also known as Polyox WSR® N-3000 available from Union Carbide, polyacrylic acid, polyvinyl alcohol, potassium alginate, potassium aluminum polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacrylate, sodium silicoaluminate, sodium sulfate, stearalkonium bentonite, stearalkonium hectorite, stearyl alcohol, tallow alcohol, TEA-hydrochloride, tragacanth gum, tridecyl alcohol, tromethamine magnesium aluminum silicate, wheat flour, wheat starch, xanthan gum, and mixtures thereof.

The concentration of gelling agent can be adjusted to change the viscosity of the gel. For example, in some embodiments the formulation includes less than 1%, or about 1%, 10%, 20%, 30%, 40%, 50%, 60%, or 70% 80% w/w of a gelling agent. Alternatively, the gelling agent can be in a range of 0.1-80% w/w. In a preferred embodiment, the gelling agent is about 1% w/w of a carbomer, for example CARBOMER 940.

Suitable solvents in the liquid vehicle include, but are not limited to, diglycol monoethyl ether; alklene glycols, such as propylene glycol; dimethyl isosorbide; alcohols, such as isopropyl alcohol, ethanol, and dehydrated alcohol. The concentration of the solvent can also be adjusted. For example, in some embodiments the formulation includes less than 1%, or about 1%, 10%, 20%, 30%, 40%, 50%, 60%, or 70% v/v of solvent. Alternatively, the solvent can be in a range of about 1-70% v/v. The solvents are typically selected for their ability to dissolve the drug. In a preferred embodiment the solvent is a dehydrated alcohol, such as absolute ethanol.

Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

The gel may also contain a preservative. Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

Transdermal formulations can be prepared to provide sustained or extended release of the active agent.

In some embodiments, the active ingredient is formulated in a hydroalcoholic gel. The most preferred embodiment includes danazol, water, dehydrated alcohol, and a penetration enhancer. Additional components of the hydroalcoholic gel may include one or more gelling agents such as carbomer 940, and excipients or carriers such as propylene glycol, glycerin, and PEG 400.

Additional agents can be added to the formulation to improve the solubility of the drug. In some embodiments, the penetration enhancer increases the solubility of the drug, and improves transdermal delivery of the drug across the skin, in particular across the stratum corneum. In a preferred embodiment, the penetration enhancer is N-methyl-2-pyrrolidone, or 2-pyrrolidone in an effective amount to improve the solubility of danazol. In one embodiment, N-methyl-2-pyrrolidone, or 2-pyrrolidone is between about 10% and 60% w/w of the formulation, preferably between about 15% and 50% w/w of the formulation, most preferably 15% w/w of the formulation. The most preferred embodiment is hydroalcoholic gel #2 of Examples 3 and 4 described below.

E. Dosage

The compositions are administered to a patient in an amount that contains low dosages of drug. Typically the dosage in the topical formulation will be about one-tenth of the oral dosage. For danazol, the dosage range is from about 1 to 200 mg, preferably from about 10-50 mg/day. In a preferred embodiment, a single dose is between about 40 mg and 80 mg of danazol administered in about 2 g of hydroalcoholic gel. Formulations containing danazol preferably contain between about 0.01% and 25%, more preferably between about 0.5% and 10%, and most preferably between about 3% and 5% w/w danazol.

II. Methods of Administration

The formulations are preferably administered topically to the surface of the breast or chest, transported transdermally and delivered to breast tissue. The compositions are administered to treat diseases and disorders of the breast, chest and the underlying musculature. In particular, the compositions may be administered to treat benign diseases of the breast, including mastalgia, mastodynia, Mondor's disease, fibrocystic breast disease, costochondritis, mastitis, Paget's disease of the areola, fibroadenoma, breast abscess, and breast infections. Typically these will be administered at least once a day or as needed.

The present invention will be thither understood with reference to the following non-limiting examples.

EXAMPLES

Example 1

In Vitro Study of Skin Permeability with a Danazol Cream Formulation

Materials and Methods

Formulation

The danazol formulation of example 1 is danazol, USP (100 mg/dose; 46.99% of the formulation), cabopol 934 NDF (0.33 mg/dose; 0.16% of the formulation), glycerin, USP (13.33 mg/dose; 6.26% of the formulation); methylparaben, NF (0.28 mg/dose; 0.13% of the formulation); trolamine, NF (0.5 mg/dose; 0.23% of the formulation); and purified water, USP qs (98.39 mg/dose; 46.23% of the formulation).

Materials

Lucifer yellow was purchased from Molecular Probes (Eugene, Oreg.). Atenolol, caffeine, and Krebs-Ringer bicarbonate buffer were obtained from Sigma-Aldrich (St. Louis, Mo.). Blank Krebs-Ringer Bicarbonate buffer O(RB buffer) was modified by including 1.2 mM $CaCl_2$, and 10 mM HEPES at pH 7.4.

Tissue Preparation and Permeability Assay

Dermatomed human abdominal skin was obtained from Asterand Inc. (Detroit, Mich.). The donor was a 77-year-old Caucasian female. It was kept frozen at −80° C. until the time of the study. After thawing at room temperature, the skin was soaked in saline for 30 minutes, and then cut to the appropriate size (approximately 4 $cm^2$) necessary. Excess moisture and saline were wiped off. The tissue was immediately transferred to the Franz-cell diffusion chamber and clamped between the donor and receiver chambers. The exposed surface area of the Franz-cell diffusion chamber was 1.77 $cm^2$. The receiver compartment was filled with 8 mL KRB buffer. The reservoir also contained a stirring bar to mix the reservoir contents. The stirring rate was set at 10 (400 RPM). Each Franz-cell diffusion chamber was then placed in a dry block heating/stirring module. The temperature was set to maintain the tissue surface at 32° C. The formulation containing 47% of danazol (Chamber 1: 0.6846 g; Chamber 2: 0.5811 g; Chamber 3: 0.6929 g; Chamber 4: 0.6733 g; (Mean±S.D.: 0.6580±0.0519 g)) was directly rubbed into the donor compartment on the top of the skin tissue. However, the formulation was not soft because of the solid cream type formulation, and it was difficult to spread to the skin surface to cover the entire surface. The formulation was unable to be stacked to the surface tightly. For parallel control compound assessment, a dosing vehicle containing the tissue integrity marker, lucifer yellow (100 µM), the low permeability reference, atenolol (100 µM), and the high permeability reference, caffeine (100 µM) in KRB buffer (2 ml), was placed directly into the donor compartment on the top of the tissue surface (this treatment did not involve any formulation).

Samples (1.0 mL) were taken from the receiver compartment at 0, 2, 4, 8, 24, and 48 hours for formulation assays and the control assay. After taking samples, an equal volume of receiver KRB buffer was added back to replace the buffer removed. For the control assay, 200 µl of dosing solution (prior to 0 hours) was taken from the container and 200 µl of 0 and 48 hours samples were taken from the donor side of the chamber.

Sample Analysis

Lucifer yellow concentrations in the control assay were measured using a FLUOstar fluorescence plate reader (BMG Laboratories, Durham, N.C.). The excitation and emission wavelengths were 485 and 538 nm, respectively.

The test compound, danazol, and control compounds, atenolol and caffeine, were measured by LC-MS/MS. The liquid chromatography phase was carried out using a Keystone Hypersil BDC C12 30×2.0 mm i.d., 3 µm, with guard column and 25 mM ammonium formate buffer (pH 3.5), where Aqueous Reservoir (A) was 90% water, 10% buffer, and Organic Reservoir (B) was 90% acetonitrile, 10% buffer. A flow rate of 300 µL/minute was applied to a gradient program of 0.0 min: 100% A, 0% B; 1.5 min: 0% A, 100% B; 2.0 min: 0% A, 100% B; 2.1 min: 100% A, 0% B; 3.5 min: 100% A, 0% B; for a total run time of 3.5 minutes (Autosampler: 30 µL injection volume; Autosampler Wash: water/acetonitrile/2-propanol:1/1/1; with 0.2% formic acid). Mass spectroscopy was carried out using a PE SCIEX API 3000 (interface: turbo ionspray; mode: multiple reaction monitoring; method: 3.5 minute duration).

Data Analysis

For the test compound, danazol, the fluxes (nmole/cm²/hour) was calculated, because of no donor analysis, from a linear part of the slope of the cumulative amount permeating into the receiver side through a unit of surface area of the skin (nmole/cm²) as a function of time.

The following calculations were performed:

$$\text{Flux} = d[(C_r \times V_r)/A]/dt$$

where, $C_r$ is the cumulative receiver compartment concentration in nM $V_r$ is the volume of the receiver compartment, 8.0 mL A is the diffusional surface area of the exposed skin membrane, 1.77 cm².

For the QC compounds, lucifer yellow, atenolol, and caffeine, the apparent permeability coefficient ($P_{app}$) and percent recovery were calculated as follows:

$$P_{app} = (dC_r/dt) \times V_r/(A \times C_0)$$

$$\text{Percent Recovery} = 100 \times ((V_r \times C_r^{final}) + (V_d \times C_d^{final}))/(V_d \times C_0)$$

Where, dC/dt is the slope of the cumulative receiver compartment concentration versus time, µM/min.

A is the diffusional surface area of the exposed skin membrane, 1.77 cm².

$V_r$ is the volume of the receiver compartment, 8.0 mL $V_d$ is the volume of the donor compartment, 2.0 mL.

$C_r$ is the cumulative receiver compartment concentration in µM.

$C_0$ is the concentration of the donor at 0 minutes of the incubation, µM.

$C_r^{final}$ is the concentration of the receiver at the end of the incubation period, µM.

$C_d^{final}$ is the concentration of the donor at the end of the incubation period, µM.

Results

The raw data of donor and cumulative receiver concentration (µM) of quality control compounds: lucifer yellow (Table 1), atenolol (Table 2), and caffeine (Table 3), at appropriate time points, and their $P_{app}$ and percent recovery on the parallel control assay are shown in Tables 1-3 (* below the lower limit of quantification; assumed to be "0" for calculation of $P_{app}$ and % recovery).

TABLE 1

Test Compound - Lucifer Yellow Cumulative Receiver Concentration (µM)

| Sampling Side | Sampling Time (hrs.) | Replicate 1 | Replicate 2 | Replicate 3 | Mean ± S.D. |
|---|---|---|---|---|---|
| Dosing | | 111.9 | 100.4 | 99.9 | 104.0 ± 6.8 |
| Donor | 0 | 100.4 | 99.9 | 97.5 | 99.3 ± 1.6 |
| | 48 | 86.6 | 95.1 | 84.5 | 88.7 ± 5.6 |
| Receiver | 0 | 0* | 0* | 0* | 0 ± 0 |
| | 2 | 0* | 0* | 0* | 0 ± 0 |
| | 4 | 0* | 0* | 0* | 0 ± 0 |
| | 8 | 0* | 0* | 0* | 0 ± 0 |
| | 24 | 0* | 0* | 0* | 0 ± 0 |
| | 48 | 0* | 0* | 0* | 0 ± 0 |
| Papp (×10⁻⁶ cm/s) | | 0.0 | 0.0 | 0.0 | 0 ± 0 |
| % Recovery | | 83.2 | 91.4 | 81.2 | 85.3 ± 5.4 |

TABLE 2

Test Compound - Atenolol Cumulative Receiver Concentration (µM)

| Sampling Side | Sampling Time (hrs.) | Replicate 1 | Replicate 2 | Replicate 3 | Mean ± S.D. |
|---|---|---|---|---|---|
| Dosing | | 102.0 | 101.0 | 103.0 | 102.0 ± 1.0 |
| Donor | 0 | 93.6 | 91.9 | 94.7 | 93.4 ± 1.4 |
| | 48 | 96.2 | 96.2 | 83.1 | 91.8 ± 7.6 |
| Receiver | 0 | 0* | 0* | 0* | 0 ± 0 |
| | 2 | 0* | 0* | 0.003 | 0.001 ± 0.002 |
| | 4 | 0* | 0* | 0.007 | 0.002 ± 0.004 |
| | 8 | 0* | 0* | 0.022 | 0.007 ± 0.013 |
| | 24 | 0.001 | 0* | 0.110 | 0.037 ± 0.063 |
| | 48 | 0.003 | 0* | 0.212 | 0.072 ± 0.122 |
| Papp (×10⁻⁶ cm/s) | | 0.000 | 0.000 | 0.060 | 0.02 ± 0.04 |
| % Recovery | | 94.3 | 94.3 | 82.3 | 90.3 ± 6.9 |

TABLE 3

Test Compound - Caffeine Cumulative Receiver Concentration (µM)

| Sampling Side | Sampling Time | Replicate 1 | Replicate 2 | Replicate 3 | Mean ± S.D. |
|---|---|---|---|---|---|
| | Dosing (hrs.) | 110.0 | 107.0 | 109.0 | 108.7 ± 1.5 |
| Donor | 0 | 103.0 | 102.0 | 103.0 | 102.7 ± 0.6 |
| | 48 | 112.0 | 105.0 | 90.1 | 102.4 ± 11.2 |
| Receiver | 0 | 0* | 0* | 0* | 0 ± 0 |
| | 2 | 0* | 0* | 0.026 | 0.009 ± 0.015 |
| | 4 | 0.001 | 0.001 | 0.053 | 0.018 ± 0.030 |
| | 8 | 0.007 | 0.007 | 0.137 | 0.050 ± 0.075 |
| | 24 | 0.055 | 0.044 | 0.489 | 0.196 ± 0.254 |
| | 48 | 0.132 | 0.106 | 0.931 | 0.390 ± 0.469 |
| Papp (×10⁻⁶ cm/s) | | 0.040 | 0.030 | 0.240 | 0.10 ± 0.12 |
| % Recovery | | 103.6 | 97.0 | 86.3 | 95.6 ± 8.7 |

The raw data of cumulative concentration (µM) of the test compound, danazol, in the receiver side at appropriate time points, and the fluxes from the danazol test formulation are shown in Table 4 (* below the lower limit of quantification; assumed to be "0" for calculation of flux).

TABLE 4

Test Compound - Danazol Cumulative Receiver Concentration (µM)

| Sampling Side | Sampling Time | Replicate 1 | Replicate 2 | Replicate 3 | Mean ± S.D. |
|---|---|---|---|---|---|
| Receiver | 0 | 0* | 0* | 0* | 0 ± 0 |
| | 2 | 0* | 0* | 0* | 0 ± 0 |
| | 4 | 0* | 0* | 0* | 0 ± 0 |
| | 8 | 0* | 0* | 0* | 0 ± 0 |
| | 24 | 0* | 0* | 0* | 0 ± 0 |
| | 48 | 0* | 0* | 0* | 0 ± 0 |
| Flux (nmole/cm²/hrs) | | 0 | 0 | 0 | 0 ± 0 |

Tissue integrity marker, lucifer yellow, was below lower limit of quantification (LLOQ) in all receiver buffer. The $P_{app}$ of low permeable control compound, atenolol, exhibited 0.02±0.04×10⁻⁶ cm/s and that of high permeable control compound, caffeine, exhibited 0.10±0.12×10⁻⁶ cm/s. The flux of the customer's test compound, danazol, was zero in all replicate, since danazol was not detected in all receiver compartment. The results indicate that the donor used in this assay was acceptable until 48 hours on the tissue integrity assessment, since all replicate was passed by lucifer yellow permeation.

The flux of the test compound, danazol, was zero in all replicate, since danazol was not detected in all receiver compartment. One possible cause was the formulation, a solid cream type formulation, was difficult to spread on the skin surface and to cover the entire surface tightly. Another possibility is that the danazol may also have accumulated in the skin tissue and not have been released into the receiver compartment since danazol is very insoluble and lipophilic.

Example 2

In Vitro Study of Skin Permeability with Danazol Formulations

Materials and Methods

Materials

Lucifer yellow was obtained from Molecular Probes (Eugene, Oreg.). Bovine serum albumin (BSA), oleyl alcohol and propylene glycol were obtained from Sigma-Aldrich (St. Louis, Mo.). Danazol was supplied by FemmePharma. The reservoir buffer contained filtered 1% BSA in Krebs Ringer bicarbonate (KRB) buffer, which contained 10 mM HEPES and 0.015 mM sodium bicarbonate at the pH of 7.4.

Tissue

Dermatomed human breast skin was obtained from Bioreclamation Inc. (Hicksville, N.Y.). The donor was a 72 year old, Caucasian female. The dermatomed skin consists only of epidermal layer and was kept frozen at −80° C. until the time of the study.

Formulations

Danazol solubility in propylene glycol was greater than 10 mg/mL. Two different carriers were tested. One carrier was propylene glycol and the second was 5% oleyl alcohol in propylene glycol. Oleyl alcohol is known to have skin permeation enhancing properties.

The first formulation ("Formulation 1") contained propylene glycol (10 mL), lucifer yellow (25.63 mg) and danazol (100.64 mg). The second formulation ("Formulation 2") contained propylene glycol (9.5 mL), oleyl alcohol (0.5 mL), lucifer yellow (25.46 mg) and danazol (100.61 mg). Lucifer yellow was included in the formulations to monitor membrane integrity during the experiment. Each formulation was run in four replicates from the one skin donor.

Permeation Study

The skin was thawed at room temperature for approximately 30 minutes and rinsed with saline. The skin was cut into approximately 3 cm² sections, which were clamped between the donor and receiver chambers of Franz diffusion cells. The receiver chamber was filled with 8 mL of reservoir buffer. A stirring bar mixed the reservoir contents. Then 0.2 mL of a formulation was placed directly on top of the skin in the donor chamber.

Each Franz diffusion cell was placed in a dry block heating/stirring module. The temperature was set at 40° C. in order to maintain 37° C. in the reservoir. The stirring rate was set at 10 (400 RPM). Samples (0.5 mL) were taken from the receiver chamber at 2, 4, 8, 24, 32, and 48 hours and replaced with an equal volume of reservoir buffer.

For the analysis of danazol, 200 µL of reservoir sample was diluted with 400 µL acetonitrile to precipitate the albumin, and centrifuged at 10,000 RPM for 10 minutes. At the end of the 48 hours incubation, samples were collected from the donor chamber for calculating the mass balance.

Sample Analyses

Lucifer yellow concentrations were measured using a FLUOstar fluorescence plate reader (BMG Laboratories, Durham, N.C.). The excitation and emission wavelengths were 485 and 538 nm, respectively. Danazol was measured by LC/MS using electrospray ionization.

Data Analysis

Cumulative concentrations in the receiver chamber were calculated compensating for the removal and replacement of the 0.5 mL sample, as follows.

$$C_r = C_n + (0.5 \text{ mL}/8.0 \text{ mL}) \times C_{n-1} \quad \text{(Eq. 1)}$$

where $C_n$ and $C_{n-1}$ are the measured receiver concentrations at time point n, and the previous time point, n−1, respectively.

The apparent permeability, $P_{app}$, was calculated as follows:

$$\text{Flux} = (dC_r/dt) \times V_r/A \quad \text{(Eq. 2)}$$

$$P_{app} = (dC_r/dt) \times V_r/(A \times C_0) \quad \text{(Eq. 3)}$$

where, $dC_r/dt$ is the slope cumulative concentration in the receiver chamber versus time in μg/mL $V_r$ is the volume of the receiver chamber (8 mL)

A is the diffusional area of the exposed skin membrane (1.77 cm$^2$)

$C_0$ is the initial concentration of compound in the formulation in μg/mL.

Results

The amounts of danazol that permeated into and/or through the skin at different times are plotted in FIG. 1. Skin permeability of danazol was clearly enhanced in the presence of 5% oleyl alcohol.

Flux and $P_{app}$ were estimated using the slope of the cumulative concentration vs. time profiles from 8 hours to 48 hours (see FIG. 1). Flux and $P_{app}$ values are presented in Table 5.

TABLE 5

Danazol Flux and $P_{app}$ Values

|  | Danazol Flux (μg/cm$^2$/hr) | Danazol $P_{app}$ (10$^{-6}$, cm/hr) |
|---|---|---|
| Formulation 1 | 0.0034 ± 0.0015 | 0.32 ± 0.14 |
| Formulation 2 | 0.055 ± 0.016 | 4.83 ± 0.40 |

The donor chambers were sampled at the end of the 48 hour incubation period and assayed for danazol. These results are listed in Table 5. The propylene glycol carrier (Formulation 1) provided relatively low permeation as indicated by high percentages recovered in the donor compartment. This result is consistent with the results for permeation through the skin (see Table 5). However, Formulation 2, which used oleyl alcohol and propylene glycol as the carrier, delivered most of the danazol through the skin to the receiver chamber. This is indicated by the low percentages of danazol that remained in the donor chamber at 48 hours (see Table 5). Similarly, Table 5 demonstrates that a greater amount of danazol permeated into and/or through the skin with Formulation 2 than with Formulation 1. The permeability of danazol was approximately 13-fold greater using the carrier that contained 5% oleyl alcohol in propylene glycol, relative to the carrier that contained 100% propylene glycol.

TABLE 6

Danazol donor concentrations after the 48 hour incubation, and percentage remaining unabsorbed Formulation 1

|  | Skin 1 | Skin 2 | Skin 3 | Skin 4 | Average (1-3 only) |
|---|---|---|---|---|---|
| 0 hr | Not individually sampled |  |  |  | 10.90 (mg/mL) |
| 48 hr | 12.00 (mg/mL) | 9.37 (mg/mL) | 8.73 (mg/mL) | 3.47 (mg/mL) | 10.03 (mg/mL) |
| Remaining % | 110.09 | 85.96 | 80.09 | 31.83 | 92.05 |

TABLE 6-continued

Danazol donor concentrations after the 48 hour incubation, and percentage remaining unabsorbed Formulation 2

|  | Skin 5 | Skin 6 | Skin 7 | Skin 8 | Average |
|---|---|---|---|---|---|
| 0 hr | Not individually sampled |  |  |  | 13.30 (mg/mL) |
| 48 hr | 1.43 (mg/mL) | 1.50 (mg/mL) | 1.14 (mg/mL) | 1.01 (mg/mL) | 1.27 (mg/mL) |
| Remaining % | 10.75 | 11.28 | 8.57 | 7.59 | 9.55 |

Lucifer Yellow Permeation

Each skin membrane was evaluated for permeation of lucifer yellow, which provides an indication of membrane integrity. There was no permeation of Lucifer yellow detectable until after 8 or 24 hours of incubation, indicating that these skin specimens were not permeable for this polar marker compound. Lucifer yellow $P_{app}$ values were similar for the values obtained for the carriers of Formulations 1 and 2 (see Table 5 for values).

Example 3

Preparation of Various Danazol Formulations

Materials

Five topical formulations of danazol were prepared at target concentrations of 2 to 5% w/w. Placebo preparations were also made for each formulation. The formulations include: Hydro-alcoholic gels: prepared using alcohol and other water miscible organic solvents; Non-aqueous gel: prepared using water miscible organic solvents; Polyethylene glycol (PEG) ointments: water soluble ointment base.

Hydro-alcoholic gels: Two hydro-alcoholic gel formulations were prepared at 2% w/w danazol concentration. These gels were prepared using the gelling agent, Carbomer 940. No precipitation of danazol was observed on room temperature storage. First gel formulation contains only about 6% dehydrated alcohol which is used primarily to disperse the gelling agent and also to provide some cooling effect. The formulation of hydro-alcoholic gel #1 (pH 6.77) was danazol (2.0% w/w); water (10.0% w/w); PEG 400 (24.0% w/w); 2-pyrrolidone (47.1% w/w); propylene glycol (5.0% w/w); glycerin (5.1% w/w); dehydrated alcohol (6.0% w/w); and carbomer 940 (0.8% w/w) which formed a light yellow, clear viscous, fluid, smooth, and non-stringy gel. The second formulation contained about 47% alcohol which is used as a co-solvent to solubilize danazol and to provide a significant cooling effect. The formulation of hydro-alcoholic gel #2 (pH 6.63) was danazol (2.0% w/w); water (10.0% w/w); PEG 400 (15.0% w/w); 2-pyrrolidone (15.0% w/w); propylene glycol (5.0% w/w); glycerin (5.0% w/w); dehydrated alcohol (46.9% w/w); carbomer 940 (1.0% w/w); and 1% aqueous solution of tromethamine to adjust pH which formed a light yellow, clear, thick, smooth, and non-stringy gel.

Non-aqueous gel prepared using water miscible organic solvents: The non-aqueous gel formulation containing 4% w/w danazol was prepared using the gelling agent, hydroxypropyl cellulose (Klucel). No precipitation of danazol was observed on room temperature storage. The formulation of the non-aqueous gel (pH 7.12) was danazol (4.0% w/w); PEG 400 (39.9% w/w); 2-pyrrolidone (10.0% w/w); propylene glycol (8.0% w/w); glycerin (10.1% w/w); dehydrated alcohol (26.8% w/w); and klucel (1.25% w/w) which formed a light yellow, clear, smooth, and non-stringy gel.

PEG ointments: Two PEG ointment formulations were prepared using different concentrations of PEG 400 and PEG 3350 based on the method outlined in USP. The two formulations were prepared at 3% and 5% w/w danazol concentrations, respectively. No danazol crystals were observed through microscopic examination on room temperature storage. The formulation of PEG Ointment #1 was danazol (3.1% w/w); PEG 400 (51.9% w/w); PEG 3350 (20.0% w/w); 2-pyrrolidone (15.1% w/w); and glycerin (10.0% w/w) formed a light yellow, opaque ointment. The formulation of PEG Ointment #2 was danazol (5.0% w/w); PEG 400 (45.0% w/w); PEG 3350 (34.9% w/w); 2-pyrrolidone (10.0% w/w); and glycerin (5.0% w/w) formed a light yellow, opaque, very firm ointment.

All of these formulations contain danazol at the desired target concentration range of 2 to 5% w/w. These formulations are observed to have a good feel upon topical skin application.

Example 4

Danazol Flux Using Various Topical Formulations

Materials and Methods
  Materials
  Lucifer yellow was purchased from Molecular Probes Eugene, Oreg.). Bovine serum albumin BSA), Krebs Ringer bicarbonate buffer, atenolol, and antipyrine were obtained from Sigma-Aldtich (St. Louis, Mo.). The reservoir buffer consisted of filtered 1% BSA in Krebs Ringer bicarbonate (KRB) buffer containing 10 mM HEPES and 0.015 mM sodium bicarbonate at a pH of 7.4.
  Tissue
  Dermatomed human breast skin was obtained from Bioreclamation Inc. (Hicksville, N.Y.). The donor was a 72 year old, Caucasian female. The dermatomed skin consists only of epidermal layer and was kept frozen at −80° C. until the time of the study.
  Dosing Vehicles
  The danazol gels were Hydro-alcoholic gel #1 (active), Hydro-alcoholic gel #2, and PEG ointment #1. To these vehicles, prior to dosing, lucifer yellow, caffeine and atenolol were added at 2.5 mg/mL. Each dosing vehicle was run in three replicates.
  Non-Specific Biuduig Studies
  Non-specific binding to the Franz chamber apparatus was assessed by exposing the danazol to the apparatus without tissue (blank apparatus). The concentration of danazol was 10 µg/ml. The concentration in the apparatus was determined after 0 and 180 minutes of incubation to mimic a skin permeation experiment. The medium was filtered 1% bovine serum albumin (BSA) in Krebs Ringer bicarbonate (KRB) buffer containing 10 mM HEPES and 0.015 mM sodium bicarbonate at a pH of 7.4.
  The experiment was done in triplicate. The danazol concentrations in the buffer did not change significantly during the course of the experiment, indicating that there was no significant loss to the apparatus as outlined below:

| Time (mid) | Average Measured Concentration (µg/ml) ± STD (N = 3) |
| --- | --- |
| 0 | 8.9 ± 0.3 |
| 180 | 8.5 ± 0.3 |

Permeation Study
The skin was thawed at room temperature for approximately 30 minutes and rinsed with saline. The skin was cut into approximately 3 cm² sections, and the sections were clamped between the donor and receiver chambers of Franz diffusion cells. The receiver compartment was filled with 8 mL of reservoir buffer and contained a stiring bar to mix the reservoir contents. The dosing gel vehicle (0.2 mL) was then placed directly on top of the skin in the donor compartment. Each Franz diffusion cell was placed in a dry block heating/stirring module. The temperature was set at 40° C. in order to maintain 37° C. in the reservoir. The stirring rate was set at 10 (400 RPM). Samples (1 mL) were taken from the receiver compartment at 0, 2, 4, 8, 24, 32, and 48 hours and replaced with an equal volume of reservoir buffer. For the analysis of danazol, 100 µL aliquots of the receiver samples were placed in a 2-mL conical bottom 96-well plate, and 400 µL of acetonitrile was added to each sample. The plate was centrifuged at 3500 rpm for 15 minutes to precipitate the protein in the receiver samples. The 400 µL of supernatant was transferred to a new plate and the organic was evaporated at 45° C. for 30 min before reconstitution with 100 µL of 10% acetonitrile in deionized water. The samples were vortexed for 5 minutes and 15 µL was injected on to the LC/MS. At the end of the 48 hours of incubation, all gel was collected from the donor and analyzed.

Sample Analysis
Lucifer yellow concentrations were measured using a FLUOstar fluorescence plate reader BMG Laboratories, Durham, N.C.). The excitation and emission wavelengths were 485 and 538 nm, respectively. Danazol was measured by LC/MS using electrospray ionization. The liquid chromatography phase was carried out using a Hypersil BDS C18 30×2.1 mm i.d., 3µ column (Thermo Electron Corporation) where Aqueous M.P. (A) was water and Organic M.P. (B) was acetonitrile. A flow rate of 300 µL/min was applied for a total run time of 6 minutes. (Autosampler 15 µl Inj. Vol.; Autosampler wash: water/acetonitrile/2-propanol:1/1/1; with 0.2% formic acid). Mass spectroscopy was carried out using an APCI 3000, Triple Quadrupole LC/MS/MS (interface: heated nebulizer; mode: multiple reaction monitoring; method: 6.0 minute duration.

Data Analysis
Cumulative concentrations in the receiver chamber were calculated compensating for the removal and
replacement of the 1.0 mL sample, as follows.
where, $$C_r = C^n + (1 \text{ mL}/8.0 \text{ mL}) \times C^{n-1}$$

$C_r$ is the cumulative concentration in the receiver compartment
$C^n$ is the measured receiver concentration at time point n
$C^{n-1}$ is the measured receiver concentration at the previous time point, n−1
The apparent permeability, $P_{app}$, and Flux were calculated as follows:

$$\text{Flux} = (dC_r/dt) \times V_r/A$$

$$P_{app} = (dC_r/dt) \times V_d/(A \times C_0)$$

where,
$(dC_r/dt)$ is the slope of the cumulative concentration in the receiver compartment versus time
$V_r$ is the volume of the receiver compartment, 8 mL
$V_d$ is the volume of the donor compartment, 0.20 mL
A is the diffusional area of the exposed skin membrane, 1.78 cm²

$C_0$ is the initial concentration of compound in the dosing vehicle in pg/mL

For the test article danazol and other assayed compounds, the linear portion of the cumulative concentration in the receiver compartment versus time was used to calculate the $P_{app}$ and Flux value.

Results

Danazol Permeation

Figure 2:
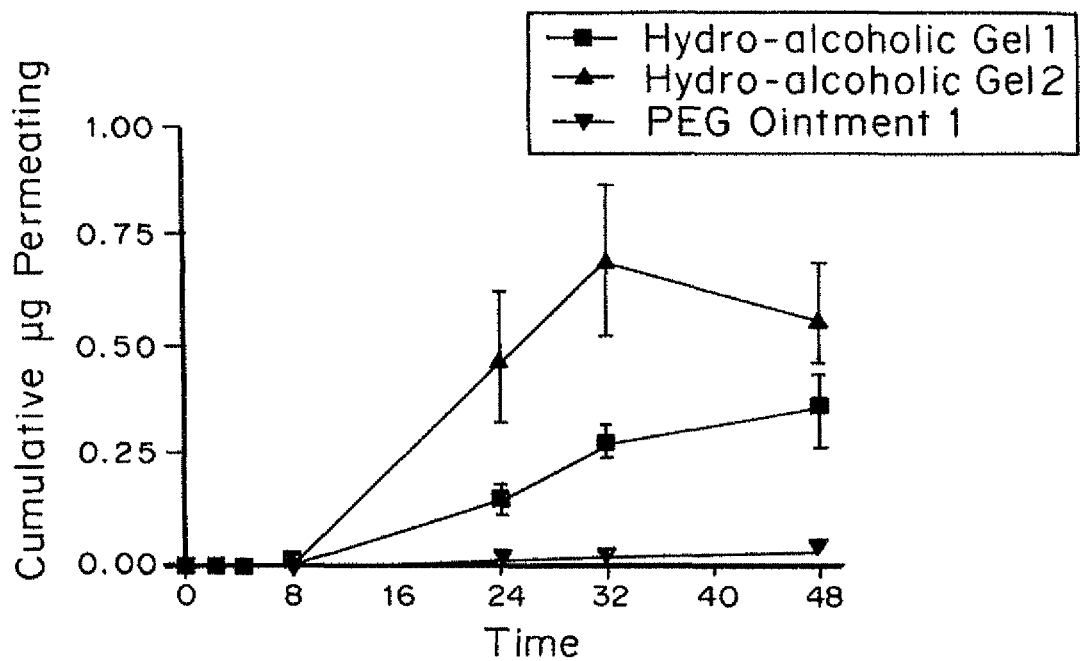
FIG. 2 is a graph of cumulative amount of danazol permeating through the breast skin (μg) over time (hours) for three different formulations: two formulations containing a hydroalcoholic gel carrier (hydro-alcoholic gel 1 (—■—); hydro-alcoholic gel 2 (—▲—)), and one containing a propylene glycol (PEG) ointment carrier (PEG Ointment 1 (—▼—)).

A plot of the amount of danazol permeating through the breast skin vs. time is given in FIG. 2. $P_{app}$ (Table 7) and Flux (Table 8) values of danazol are presented in Tables 7 and 8 (* values were below the lowest limit of quantitation, therefore $P_{app}$ was not calculated).

TABLE 7

Danazol $P_{app}$ Values

| Dosing Vehicle | Papp ($10^{-6}$, cm/hr) Replicate 1 | Papp ($10^{-6}$, cm/hr) Replicate 2 | Papp ($10^{-6}$, cm/hr) Replicate 3 | Average Papp ($10^{-6}$, cm/hr) ± STD |
|---|---|---|---|---|
| hydro-alcoholic gel #1 | 1.153 | 2.418 | 1.566 | 1.712 ± 0.645 |
| hydro-alcoholic gel #2 | 2.752 | 6.335 | 3.537 | 4.208 ± 1.884 |
| PEG Ointment #1 | 0.131 | 0.177 | 0.087 | 0.131 ± 0.045 |

TABLE 8

Danazol Flux Values

| Dosing Vehicle | Flux (µg/cm²/hrs) Replicate 1 | Flux (µg/cm²/hrs) Replicate 2 | Flux (µg/cm²/hrs) Replicate 3 | AverageFlux (µg/cm²/hrs) ± STD |
|---|---|---|---|---|
| hydro-alcoholic gel #1 | 0.027 | 0.062 | 0.036 | 0.041 ± 0.018 |
| hydro-alcoholic gel #2 | 0.083 | 0.189 | 0.111 | 0.127 ± 0.055 |
| PEG Ointment #1 | 0.004 | 0.005 | 0.002 | 0.004 ± 0.001 |

TABLE 9

$P_{app}$ Values for Lucifer Yellow, Atenolol, and Caffeine

| Dosing Vehicle | Average Lucifer Yellow Papp ($10^{-6}$, cm/hr) ± STD (N = 3) | Average Atenolol Papp ($10^{-6}$, cm/hr) ± STD (N = 3) | Average Caffeine Papp ($10^{-6}$, cm/hr) ± STD (N = 3) |
|---|---|---|---|
| hydro-alcoholic gel #1 | 0.0020 ± 0.0026 | 0.0016 ± 0.0024 | 0.0498 ± 0.0098 |
| hydro-alcoholic gel #2 | 0.0010 ± 0.0004 | 0.0014 ± 0.0014 | 0.1188 ± 0.0717 |
| PEG Ointment #1 | NC* | 0.00005 ± 0.00003 | 0.0108 ± 0.0009 |

Lucifer yellow, caffeine and atenolol $P_{app}$ values are presented in Table 9
(*values were below the lowest limit of quantitation, therefore $P_{app}$ was not calculated).

The donor chambers were sampled at the end of the 48-hour incubation period and assayed for danazol. These results are given in Table 10. The propylene glycol vehicle provided relatively low permeation as indicated by high percentages recovered in the donor compartment, which is consistent with the results for permeation through the skin. After dosing with the oleyl alcohol/PG vehicle, only low percentages remained in the donor compartment at 48 hours, indicating extensive permeation into and/or through the skin.

TABLE 10

Danazol Donor Concentrations After 48-hour Incubation and % Remaining Unabsorbed

| Time (Hr.) | Replicate 1 | Replicate 2 | Replicate 3 | Average |
|---|---|---|---|---|
| Hydro-alcoholic Gel #1 (µg/mL, $10^3$) | | | | |
| 0 | 23.1 | 25.5 | 22.7 | 23.8 |
| 48 | 2.46 | 6.96 | 14.3 | 7.91 |
| % Remaining | 10.6 | 27.3 | 63 | 33 |
| Hydro-alcoholic Gel #2 (µg/mL, $10^3$) | | | | |
| 0 | 30.1 | 29.8 | 31.3 | 30.4 |
| 48 | 6.84 | 3.4 | 2.14 | 4.13 |
| % Remaining | 22.7 | 11.4 | 6.8 | 14 |
| PEG Ointment #1 (µg/mL, $10^3$) | | | | |
| 0 | 29.4 | 29.5 | 28 | 29 |
| 48 | 20.4 | 11.5 | 15 | 15.6 |
| % Remaining | 69.4 | 39 | 53.6 | 54 |

Caffeine and atenolol represent highly absorbed and moderately absorbed reference compounds, respectively. For each tested tissue, the reference compounds had Papp values with the expected rank order of caffeine greater than atenolol. In addition, Papp values of lucifer yellow were comparable to Papp values of atenolol. Also, there was no permeation of lucifer yellow detectable until after 8 or 24 hours of incubation, which attests to the integrity of the tissue. The permeability of danazol was higher when applied in Hydio-alcoholic gels compared to PEG ointment. The $P_{app}$ and Flux rank order of danazol was: Hydro-alcoholic gel #2 greater than Hydro-alcoholic gel #1 greater than PEG ointment.

Example 5

Topical Danazol Gel is Non-Irratitating

Materials and Methods

Test Animals

Animals were received from Milbrook Breeding Labs, Amherst, Mass. Following an equilibration period of at least one week, six healthy New Zealand White rabbits (approximately 3 months old) were selected for this test from a larger group without conscious bias. Pretest body weight range was 2.5-3.1 kg. The animals were identified by cage notation and a uniquely numbered metal eartag. The animals were housed 1/cage in suspended cages. Bedding, placed beneath the cages, was changed at least three times/week. Fresh PMI Rabbit Chow (Diet #5321) was provided daily. Water was available ad libitum. The animal room, reserved exclusively for rabbits on acute tests, was temperature controlled, had a 12 hour light/dark cycle and was kept clean and vermin free.

Site Preparation

Prior to application of the test article, the back and sides of each animal were clipped free of hair. The upper trunk of each animal was abraded with a bent tip needle (sites 1 and 2). Three abrasions, approximately 2-3 cm apart, extending the length of the exposure site were made. The abrasions were sufficiently deep to penetrate the stratum corneum, but not deep enough to produce bleeding. The lower trunk of each animal remained intact.

Dosing

The test articles were used as received and dosed by volume, 0.5 ml/site, for a total dose of 1.0 ml of each test article per rabbit. Each test article was applied to two areas, 1 intact and 1 abraded, on the prepared site, on the back of each of six rabbits: Site 1 (abraded)—danazol gel (2% danazol in 1.80 mg methyl parabens per gram gel); Site 2 (abraded)—placebo control (1.74 mg methyl parabens per gram gel); Site 3 (intact)—danazol gel (2%); Site 4 (intact)—placebo control.

The test articles were placed under 2.5×2.5 cm, 4 ply, surgical gauze patches which were secured with non-irritating adhesive tape. The torso was wrapped with plastic in an occlusive manner which was secured with non-irritating adhesive tape. The sites were occluded for 24 hours at which time the patches were removed. Residual test article was removed from the test site by gentle wiping at the end of the exposure period, prior to scoring for dermal reactions.

Type and Frequency of Observations

Animals were observed for skin reactions at 24 and 72 hours following application of the test articles. Erythema and edema were a numeric score (0-4) according to the numerical Drake technique (Draize, et al., *J. Pharm. Exp. Ther.* 82:377-390 (1944)): Erythema and Eschar—No erythema (0); Very slight erythema, barely perceptible (1); Well defined erythema (2); Moderate to severe erythema (3); Severe erythema (beet redness) to slight eschar formation (injuries in depth) (4); Edema—No edema (0); Very slight edema, barely perceptible—(1); Slight edema (edges of area well-defined by definite raising) (2); Moderate edema (raised approximately 1.0 mm) (3); Severe edema (raised more than 1.0 mm, extending beyond the area of exposure) (4). Body weights were recorded pretest. The general health of the animals was monitored at each observation time.

Analysis of Data

The Primary Irritation Index was calculated for each test article by adding the mean values (6 rabbits) for erythema/eschar and edema on intact and abraded skin at 24 and 72 hours (a total of 8 values) and dividing the sum by 4. A primary Irritant is defined as a substance which is not corrosive but which results in an empirical score of 5 or more (16 CFR 1500.3(c)(4)).

Results

Dermal Observations:

Danazol (2%)—intact and abraded: There was no erythema ("0") or edema ("0") noted at any time period. All measurements of erythema and edeam on sites 1, 2, 3, and 4 of all tested animals registered "0" according to the Drake technique. Therefore the Primary Dermal Irritation Index (PII) is zero (0).

Placebo—intact and abraded: There was no erythema or edema noted at any time period. Therefore the Primary Dermal Irritation Index (PII) is zero (0).

Systemic Observations

There were no abnormal physical signs noted during the observation period.

The Primary Irritation Index for each test article is 0. Therefore, danazol gel (2%) and Placebo Gel are not dermal irritants as defined in 16 CFR 1500.3(c)(4).

Those skilled in the art will recognize, or be able to ascertain using no more than routine experimentation, many equivalents to the specific embodiments of the invention described herein. Such equivalents are intended to be encompassed by the following claims.

We claim:

1. A method for treating a benign disease or disorder of the breast, chest or underlying musculature comprising
    topically administering to the breast of a patient in need thereof a drug formulation comprising
    a drug selected from the group consisting of an luteinizing hormone-releasing hormone (LHRH), danazol, and bromocriptine in an amount effective to provide regional, not systemic, relief from benign diseases or disorders of the breast, the drug dissolved or suspended in a hydroalcoholic pharmaceutical carrier comprising a N-methyl-2-pyrrolidone or 2-pyrrolidone, transdermal penetration enhancer to promote delivery of the drug across the stratum corneum.

2. The method of claim 1 wherein the carrier is selected from the group consisting of a gel, ointment, lotion, emulsion, cream, foam, mousse, liquid, spray, and aerosol.

3. The method of claim 2 comprising a solubilizing agent that improves the solubility of the drug.

4. The method of claim 3 wherein the solubilizing agent is also the penetration enhancer.

5. The method of claim 3 wherein the drug is in solution.

6. The method of claim 1, wherein the carrier is a hydroalcoholic gel.

7. The method of claim 6 wherein the drug is danazol.

8. The method of claim 1, wherein the drug formulation provides a dosage effective to treat benign diseases of the breast.

9. The method of claim 8 wherein the dosage is between about 40 mg and 80 mg of danazol/day.

10. The method of claim 1 wherein the benign disease of the breast is selected from the group consisting of mastalgia, mastodynia, Mondor's disease, fibrocystic breast disease, costochondritis, mastitis, Paget's disease of the areola, fibroadenoma, breast abscess, and breast infections.

11. The method of claim 10 wherein the drug formulation provides a dosage effective for regional treatment.

12. The method of claim 11 wherein the region is the breast, areola, and underlying musculature of the chest.

13. The method of claim 11 wherein the drug is danazol, the carrier is a hydroalcoholic gel, and the penetration enhancer is N-methyl-2-pyrrolidone or 2-pyrrolidone.

* * * * *

UNITED STATES PATENT AND TRADEMARK OFFICE
CERTIFICATE OF CORRECTION

| | |
|---|---|
| PATENT NO. | : 9,173,836 B2 |
| APPLICATION NO. | : 12/871678 |
| DATED | : November 3, 2015 |
| INVENTOR(S) | : Gerianne Tringali DiPiano, Peter Kevin Mays and John Ziemniak |

It is certified that error appears in the above-identified patent and that said Letters Patent is hereby corrected as shown below:

In the Claims:

Claim 1, column 20, line 17, replace "an luteinizing" with --a luteinizing--.

Signed and Sealed this
Fifth Day of April, 2016

Michelle K. Lee
*Director of the United States Patent and Trademark Office*